(12) United States Patent
Li et al.

(10) Patent No.: US 10,466,150 B2
(45) Date of Patent: Nov. 5, 2019

(54) ELECTROMAGNETIC INDUCTION TYPE HOPKINSON TENSION-COMPRESSION BAR LOADING DEVICE AND EXPERIMENT METHOD

(71) Applicant: Northwestern Polytechnical University, Shaanxi (CN)

(72) Inventors: Yulong Li, Shaanxi (CN); Hailiang Nie, Shaanxi (CN); Tao Suo, Shaanxi (CN); Zhongbin Tang, Shaanxi (CN)

(73) Assignee: Northwestern Polytechnical University, Shaanxi (CN)

( * ) Notice: Subject to any disclaimer, the term of this patent is extended or adjusted under 35 U.S.C. 154(b) by 0 days.

(21) Appl. No.: 15/735,069

(22) PCT Filed: Aug. 10, 2016

(86) PCT No.: PCT/CN2016/094336
§ 371 (c)(1),
(2) Date: Dec. 8, 2017

(87) PCT Pub. No.: WO2017/101464
PCT Pub. Date: Jun. 22, 2017

(65) Prior Publication Data
US 2019/0033188 A1 Jan. 31, 2019

(30) Foreign Application Priority Data
Dec. 18, 2015 (CN) .......................... 2015 1 0956545

(51) Int. Cl.
*G01N 3/317* (2006.01)
*G01L 5/00* (2006.01)
*G01N 3/08* (2006.01)

(52) U.S. Cl.
CPC ................ *G01N 3/317* (2013.01); *G01L 5/00* (2013.01); *G01N 3/08* (2013.01);
(Continued)

(58) Field of Classification Search
USPC .......................................................... 701/44
See application file for complete search history.

(56) References Cited

U.S. PATENT DOCUMENTS

2004/0073385 A1    4/2004   Miyamoto et al.

FOREIGN PATENT DOCUMENTS

| CN | 102279261 | 1/2013 |
|----|-----------|--------|
| CN | 103926138 | 7/2014 |

(Continued)

OTHER PUBLICATIONS

International Application No. PCT/CN2016/094336, International Search Report dated Oct. 27, 2016, 3 pgs.

(Continued)

*Primary Examiner* — Maceeh Anwari
(74) *Attorney, Agent, or Firm* — Schwegman Lundberg & Woessner, P.A.

(57) ABSTRACT

An electromagnetic induction type Hopkinson pressure/tension bar loading device and experiment method therefor. The device not only can generate compression stress waves but also can generate tension stress waves through the electromagnetic induction principle, and is applied to the loading of a Hopkinson tension bar and a pressure bar. Thus, the loading systems for a Hopkinson tension bar and a pressure bar can simultaneously achieve the strain rate and strain range, which the traditional split Hopkinson bar experiment cannot reach, on the same device, so that the Hopkinson bar experiment technology is standardized, and the experiment devices for a tension bar and a pressure bar are integrated, thereby reducing complexity and floor space of equipment.

20 Claims, 6 Drawing Sheets

(52) U.S. Cl.
CPC .......... *G01N 2203/005* (2013.01); *G01N 2203/0017* (2013.01); *G01N 2203/0019* (2013.01)

(56) References Cited

FOREIGN PATENT DOCUMENTS

| | | |
|---|---|---|
| CN | 103994922 | 8/2014 |
| CN | 105571961 | 5/2016 |

OTHER PUBLICATIONS

Zhang, X., et al., "Dynamic indentation experiment based on the split-Hopkinson pressure bar system", Explosion and Shock Waves, 31, (May 31, 2011), 256-262.

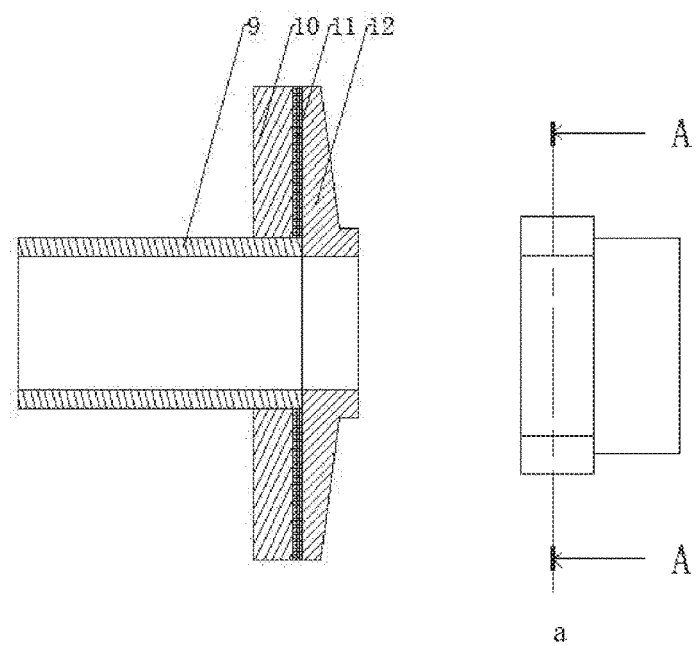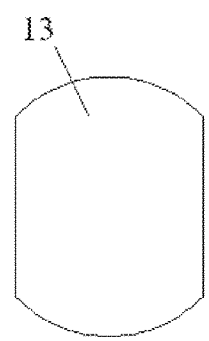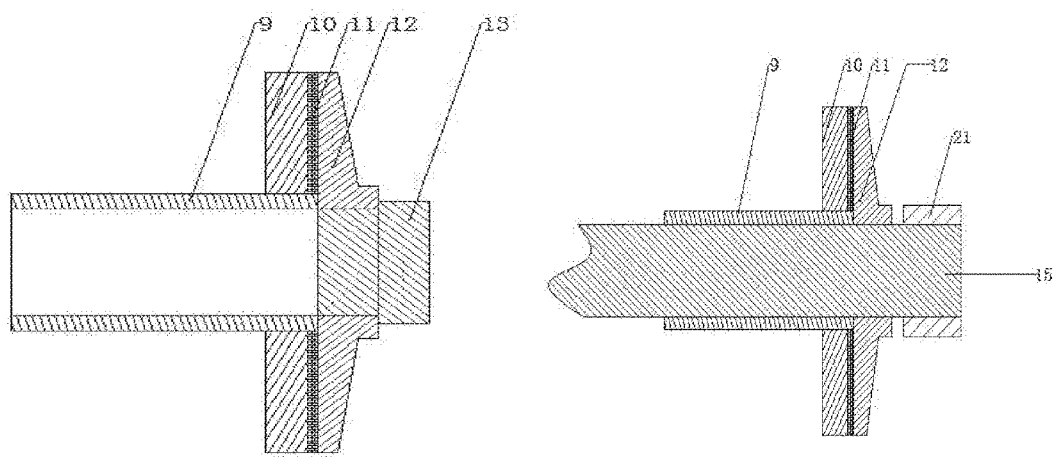
Fig. 6　　　　　　　　　　　　　　　Fig. 7
Fig. 8　　　　　　　　　　　　　　　Fig. 9

ELECTROMAGNETIC INDUCTION TYPE HOPKINSON TENSION-COMPRESSION BAR LOADING DEVICE AND EXPERIMENT METHOD

CLAIM OF PRIORITY

This application is a U.S. National Stage Filing under 35 U.S.C. 371 front international Application No. PCT/CN2016/094336, filed on Aug. 10, 2016, and published as WO 2017/101464 A1 on Jun. 22, 2017, which claims the benefit of priority to China Patent Application No. 201510956545.4, filed on Dec. 12, 2015, each of which is hereby incorporated by reference herein in its entirety.

TECHNICAL FIELD

The present invention relates to a stress wave generating device and method for testing dynamic mechanical properties of materials, particularly to a stress wave generating device and method based on an electromagnetic force. The device may be used as a stress wave input device of split Hopkinson tension bar and pressure bar.

BACKGROUND

At present, the most widely used technologies for measuring the mechanical properties of materials at a high strain rate in the field of material science are split Hopkinson pressure bar technology and tension bar technology. The basic principle of this method is that a short sample is placed between two tension bars or pressure bars, tension stress waves or compression stress waves are input to an incident bar in a certain way to load the sample. Meanwhile, pulse signals are recorded by strain gages which are pasted on the tension bars or pressure bars and have a certain distance away from one end of each bar. If the tension bars or pressure bars remain in an elastic state, the pulses in the bars will be propagated undistortedly at the elastic wave speed. Thus the strain gages pasted on the tension bars or pressure bars may measure the change of the load acting on the ends of the bars over time.

For a Hopkinson pressure bar, a common way to generate incident waves is to shoot an impact bar at high speed through an air gun and generate incident pulses by coaxial collision with the incident bar. This method has the disadvantages that the installation locations of the impact bar in the air gun are different in each shoot and it is difficult to determine the correlation between impact speed and air pressure; therefore, it is not able to accurately control the amplitude of the incident waves and it is required to do many experiments to get a desired strain rate. Secondly, for an experiment with an oversized span of strain rate, there is a need to change the length of the impact bar to obtain different strain rates due to the limitation of the air pressure of the air gun; the higher the strain rate is, the shorter the impact bar is needed, and the shorter the stress waves in the experiment are; this limits the range of strain and makes the experiment complex. What's more, as there is a lower limit to the shooting speed of the impact bar, some lower strain rates (e.g. a strain rate of 10 $s^{-1}$) in the experiment cannot be obtained by a traditional Hopkinson pressure bar. Because different experimental systems have different parameters, it is an international difficult problem to standardize the experimental technology of the split Hopkinson pressure bar.

For a Hopkinson tension bar, the commonly used loading method is that the impact bar of the tension bar is made into a hollow tube; the impact tube is shot at a high speed by the air gun; when the impact tube moves to the end of an incident bar, the impact tube collides with the lug boss on the incident bar end and generates a series of compression waves which are propagated to the lug boss end of the incident bar and reflected by the free end as tension waves; the sample is loaded by the tension waves through the incident bar. However, this loading method has many disadvantages: 1. the impact bar is shot from one end of the incident bar to the other end, so the incident bar is in an unsupported free state at the section from the lug boss on the incident bar to the air gun, and thus the incident bar is easy to bend; 2. this design limits the length of the impact tube to be about 500 mm, so the wavelength of the generated incident waves is about 0.2 ms, but for a ductile material and a low strain rate experiment, incident waves with a longer wavelength are required; 3. the impact tube is very inconvenient to replace; and 4. due to the limitation of the wall thickness of the impact tube, a very high air pressure is needed to accelerate the impact tube. Many scholars have proposed different design ideas: 1. add a lug boss at one end of the impact tube to increase the shooting speed of the impact tube, but the waveform generated by this method is affected by the lug boss and no longer regular; 2. use a hollow incident bar to allow the impact bar to pass through the incident bar, and this makes it difficult to reshape the waveform.

Because of the different shapes of the impact bar and the different positions of the air gun, the traditional Hopkinson pressure bar and tension bar loading systems cannot be realized on the same device.

In 1960s, in order to solve the problem of normal riveting, Boeing designated HuberASchmitt et al. to take the lead to research electromagnetic riveting technology, and a patent for a strong impact electromagnetic riveting apparatus was applied in 1968. Low-voltage electromagnetic riveting technology is developed successfully by Zieve Peter in 1986, which solves the problems in the riveting quality, promotion and application of high-voltage riveting technology, thus making electromagnetic riveting technology develop rapidly. Electromagnetic riveting technology has been applied in the manufacturing of Boeing and Airbus series aircraft. Today, low-voltage electromagnetic riveting technology has developed and become mature, and the magnitude and duration of riveting force may be controlled accurately. The technical principle of electromagnetic riveting is that a coil and a stress wave amplifier are added between a discharge coil and a workpiece. When a discharge switch is switched off, a primary coil generates a strong magnetic field around the coil by the rapidly changing impact current. A secondary coil coupled with the primary coil generates an induced current under the action of the strong magnetic field, and then generates an eddy current magnetic field; the two magnetic fields interact to generate an eddy current repulsion force which is transferred to a rivet through an amplifier to shape the rivet. The eddy current force has a very high frequency and is transmitted in the form of stress waves in the amplifier and the rivet, so electromagnetic riveting is also called stress wave riveting. If the principle of an electromagnetic riveting gun is applied to the split Hopkinson pressure bar to replace the air gun and impact bar in the traditional split Hopkinson pressure bar and generate stress waves by electromagnetic repulsion directly, it will be possible to standardize the experimental technology of the split Hopkinson pressure bar. In addition, the pulse width of the stress waves generated by electromagnetic induction may be adjusted by circuit parameters, and the pulse width may reach millisecond level, so some low strain rates lower than $10^2$/s) which cannot be loaded by the traditional Hopkinson bar may be loaded. In the patents with application numbers of 201420098605.4 and 201410161610.X, a device solution and experiment method where an electromagnetic riveting apparatus is directly applied to a Hopkinson pressure bar device is proposed; however, the waveform obtained by this method has limitations; in the inventions with application numbers of 201410173843:1 and 201410171963.8 respectively, two experiment devices and use methods which may be applied to both a Hopkinson tension bar and a Hopkinson pressure bar are proposed, however, the structures of the two solutions are relatively complex and traditional waveform shaping technology cannot be applied to tension. In the invention with application number of 201510051071, a primary coil structure and use method for electromagnetic stress wave generator is proposed to increase the variation range of the amplitude and pulse width of the waves generated by the electromagnetic stress wave generator.

SUMMARY

In order to overcome the defects of existing technologies such as that the amplitude of incident waves is uncontrollable, the operation is complex, the range of strain is limited and some low strain rate experiments cannot be realized, and to overcome the disadvantage of tension and compression loading devices that cannot be unified, the present invention proposes an electromagnetic induction type Hopkinson pressure/tension bar loading device and experiment method thereof.

The present invention comprises a power supply, a capacitor charger and a loading gun. A power supply part of the existing electromagnetic riveting apparatus is used by the capacitor charger, and a positive electrode output line of the output of the capacitor charger is connected with a positive electrode line of the loading gun and a negative pole output line of the output of the capacitor charger is connected with a negative electrode line of the loading gun. The loading gun comprises a loading gun housing, a primary coil, a centering tube, a secondary coil, an insulation layer and an amplifier. The primary coil and the secondary coil are mounted on the centering tube in sequence, and one end surface of the secondary coil is made to be adjacent to a locating end surface of the centering tube. The other end surface of the secondary coil is made to be adjacent to and freely fitted with one end surface of the primary coil. The centering tube on which the primary coil and the secondary coil are mounted is put in the middle section in the loading gun housing, the amplifier is installed at one end of the centering tube, and the insulation layer is mounted between the internal end surface of the amplifier and the end surface of the secondary coil. The primary coil, the secondary coil, the amplifier and the centering tube are all coaxial to the loading gun housing. One end of the centering tube is in threaded connection with the secondary coil. When a Hopkinson compression experiment is performed, a connection section of a compression head is put in an internal threaded hole of the amplifier, and the compression head is in threaded connection with the amplifier. The internal end surface of a compression wave output section of the compression head is in contact with the incident bar, thus transmitting the stress waves into the incident bar. When a Hopkinson tension experiment is performed, the end, with an external thread, of the incident bar penetrates through the through holes of the centering tube and the amplifier in sequence, and is in threaded connection with the lug boss at one side of the stress wave output section of the amplifier. When the compression stress waves transmitted from the stress wave output section of the amplifier enter the lug boss, the compression stress waves are reflected by the free end surface of the lug boss as tension waves and enter the incident bar to form the incident waves of the Hopkinson tension bar.

The primary coil of the loading gun is wound around a core with an I-shaped cross section using a wide copper strip or a copper conducting wire, and every two turns of the copper strip are separated from each other by an insulation material. The external diameter of the primary coil is identical to the internal diameter of the loading gun housing, and after the primary coil is put in the loading gun housing, the primary coil and the loading gun housing are in interference fit. A through hole is formed at the center of the core of the primary coil to allow the centering tube to freely penetrate.

The secondary coil is a copper disk, and is provided with a threaded through hole matched with the centering tube in the center thereof.

The internal surface of the central hole of the amplifier is a threaded surface matched with the external thread of the compression head. The internal diameter of the central hole of the amplifier is slightly larger than the external diameter of the incident bar of the Hopkinson tension bar, and after the incident bar of the Hopkinson tension bar is put in the central hole, the incident bar of the Hopkinson tension bar and the central hole are clearance fit. The external circumference surface of the amplifier is of a step shape, comprising isometric sections at both ends of the amplifier and a conic section at the center of the amplifier. For the isometric sections at the two ends of the amplifier, the isometric section having the maximum external diameter at one end of the amplifier is a stress wave receiving section; and the isometric section having the minimum external diameter at the other end of the amplifier is a stress wave output section. The conic section that transitionally connects the two isometric sections forms a stress wave amplification reflection section of the amplifier. The external diameter of the stress wave receiving section of the amplifier is the same as that of the secondary coil. The ratio of the diameter of stress wave receiving section of the amplifier to the diameter of the stress wave output section equals to 5:2; and the ratio of the axial length of the large external diameter section of the amplifier to that of the conic section equals to 1:1.

For the compression head, the large-diameter section is the compression wave output section, and the small-diameter section is connection section. The external circumference surface of the compression wave output section is symmetrically provided with planes;

the wave impedance of the compression wave output section is identical to that of a Hopkinson pressure bar, and the wave impedance R is defined as:

$$R=\rho CA$$

where $\rho$ represents the density of material, C represents the stress wave velocity of material, and A represents the cross-sectional area.

The experiment for a Hopkinson pressure/tension bar stress wave generator based on electromagnetic force proposed in the present invention comprises a Hopkinson compression experiment and a Hopkinson tension experiment.

I. The specific process of the Hopkinson compression experiment comprises:

Step 1: Arranging equipment;

Step 2: Pasting strain gages: when the strain gage leads are arranged, the strain gage leads are first distributed in parallel with the axis of the incident bar or the transmission bar and then led out after being bent at a right angle with the axial direction so that the leads are connected with the data acquisition unit in straight line. When the strain gages are pasted, two strain gages with identical parameters are symmetrically pasted on the surfaces of the incident bar and the transmission bar by using the axis of the incident bar or the transmission bar as a symmetry axis, and the strain gage leads are welded on pins of the strain gages and connected with a Wheatstone bridge in the data acquisition system.

The arranged strain gages are pasted on the circumference at the half length of the incident bar or the transmission bar by a conventional method.

Step 3: Loading and processing data: the Hopkinson pressure/tension bar stress wave generator is connected and matched with the incident bar, the compression head is connected with the amplifier, the centering tube passes through a through hole of the primary coil, and the end, provided with the compression head, of the loading gun is close to the incident bar. The stress wave output section of the compression head is coaxially and fully fitted with the end surface of the incident bar of the Hopkinson pressure bar.

After being charged, the capacitor charger discharges to the primary coil of the loading gun to generate electromagnetic repulsion between the secondary coil and the primary coil, the electromagnetic repulsion is showed as a compression stress wave in the amplifier, the compression stress wave forms an incident wave after being amplified by the amplifier, and the incident wave is transmitted into the incident bar of the Hopkinson pressure bar through the compression head. When the incident wave is transmitted to the contact surface between the incident bar and the sample, because the wave impedances are mismatched, one part of the incident wave is reflected to form a reflected wave in the incident bar, and the other part is transmitted into the transmission bar through the sample to form a transmitted wave.

The data acquisition unit records signals of the incident wave and the reflected wave through the strain gage pasted on the incident bar, and records signals of the transmitted wave through the strain gage pasted on the transmission bar. The signals of the reflected wave and the transmitted wave recorded by the data acquisition unit are used to obtain a dynamic compression stress strain curve of a specimen by a one-wave method.

II. The specific process of the Hopkinson tension experiment comprises:

Step 1: Arranging equipment;

Step 2: Pasting strain gages: the strain gage leads are arranged according to the method in the Hopkinson compression experiment. Specifically, when the strain gage leads are arranged, the strain gage leads are first distributed in parallel with the axis of the incident bar or the transmission bar and then led out after being bent at a right angle with the axial direction so that the leads are connected with the data acquisition unit in straight line. When the strain gages are pasted, two strain gages with identical parameters are symmetrically pasted on the surfaces of the incident bar and the transmission bar by using the axis of the incident bar or the transmission bar as a symmetry axis, and the strain gage leads are welded on pins of the strain gages and connected with a Wheatstone bridge in the data acquisition system.

Step 3: Loading and collecting data: the Hopkinson pressure/tension bar stress wave generator is connected and matched with the incident bar; when the Hopkinson pressure/tension bar stress wave generator is connected with the incident bar, the centering tube passes through the through hole of the primary coil, and the amplifier and the incident bar are respectively located at both ends of the primary coil. The incident end of the incident bar passes through a through hole of the centering tube and a threaded hole of the amplifier in sequence to freely match with the threaded hole of the amplifier and the through hole of the centering tube, and the end, with an external thread, of the incident bar penetrates through the amplifier and is in threaded connection with a lug boss.

The charging voltage of the capacitor charger is set to XV, the capacitor charger is charged, and X is a specifically required voltage value and within the rated voltage of the capacitor charger. After completion of charging, the capacitor charger discharges to the primary coil of the loading gun to generate electromagnetic repulsion between the secondary coil and the primary coil, and the electromagnetic repulsion is amplified by the amplifier, is showed as compression stress wave, is reflected by the lug boss as a tension wave, and forms an incident wave of the Hopkinson tension bar. The incident wave is transmitted into the incident bar of the Hopkinson tension bar. When the incident wave is transmitted to the contact surface between the incident bar and the sample, because the wave impedances are mismatched, one part of the incident wave is reflected to form a reflected wave in the incident bar, and the other part is transmitted into the transmission bar through the sample to form transmitted wave. The shape and the amplitude of the reflected wave and the transmitted wave depend on the material property of the sample.

The data acquisition unit records the signals of the incident wave and the reflected wave through the strain gage pasted on the incident bar, and records the signals of the transmitted wave through the strain gage pasted on the transmission bar. The signals of the reflected wave and the transmitted wave recorded by the data acquisition unit are used to obtain a dynamic tension stress strain curve of material by a one-wave method.

In the present invention, the power supply part of the existing electromagnetic riveting apparatus is used by the capacitor charger, a positive electrode output line of the capacitor charger is connected with a positive electrode line of the loading gun and a negative electrode output line thereof is connected with a negative electrode line of the loading gun. The loading gun comprises an insulation layer, a loading gun housing, a primary coil, a secondary coil, an amplifier and a centering tube. When a compression test is performed, one end of the compression head is matched with the threaded hole of the amplifier, and the other end of the compression head is fitted with the incident end of the pressure bar; when a tension test is performed, the incident bar loading end of the tension bar passes through the though hole of the centering tube and the threaded hole of the amplifier and is in threaded connection with the lug boss, and the tension bar is freely matched with the threaded hole of the amplifier and the through hole of the centering tube in dimension. The primary coil, the insulation layer and the secondary coil are all mounted on the centering tube. The insulation layer is fitted with the internal surface of the amplifier, and the secondary coil is located on the inner side of the insulation layer, fitted and fixed with the amplifier, and connected with the centering tube through bolts. Through holes of two external connectors of the primary coil are provided in the circumferential surface of the same side of the loading gun housing. During installation, the primary coil is installed in the middle position of the loading gun housing, and the positive electrode line and the negative electrode line of the primary coil pass through the through holes of the external connectors in the loading gun housing. The centering tube passes through the through hole in the middle of the primary coil, and the secondary coil and the amplifier are located at one end of the loading gun housing. The external circumferential surfaces of the secondary coil, the insulation layer and the amplifier are all in clearance fit with the internal surface of the loading gun housing.

In the present invention, when the Hopkinson compression experiment is performed, the compression head is connected with the amplifier through the existing threads, the centering tube passes through the through hole of the primary coil, and the end, provided with the compression head, of the loading gun is close to the incident bar. The stress wave output section of the compression head is coaxially and fully fitted with the end surface of the incident bar of the Hopkinson pressure bar. After being charged, the capacitor charger discharges to the primary coil of the loading gun to generate electromagnetic repulsion between the secondary coil and the primary coil, the electromagnetic repulsion is showed as a compression stress wave in the secondary coil and forms an incident wave after being amplified by the amplifier, and the incident wave is transmitted into the incident bar of the Hopkinson pressure bar through the compression head. When the incident wave is transmitted to the contact surface between the incident bar and the sample, because the wave impedances are mismatched, one part of the incident wave is reflected to form a reflected wave in the incident bar, and the other part is transmitted into the transmission bar through the sample to form a transmitted wave. The shape and the amplitude of the reflected wave and the transmitted wave depend on the material property of the sample. The data acquisition unit records signals of the incident wave and the reflected wave through the strain gage pasted on the incident bar, and records signals of the transmitted wave through the strain gage pasted on the transmission bar. The signals of the reflected wave and the transmitted wave recorded by the data acquisition unit are used to obtain a dynamic compression stress strain curve of a specimen by a one-wave method.

When the Hopkinson tension experiment is performed, the centering tube passes through the through hole of the primary coil, and the amplifier and the incident bar are respectively located at both ends of the primary coil. The incident end of the incident bar of the tension bar passes through the through hole of the centering tube and the threaded hole of the amplifier to freely match with the threaded hole of the amplifier and the through hole of the centering tube, and the end, with an external thread, of the tension bar penetrates through the amplifier and is in threaded connection with the lug boss. After being charged, the capacitor charger discharges to the primary coil of the loading gun to generate electromagnetic repulsion between the secondary coil and the primary coil, the electromagnetic repulsion is showed as a compression stress wave Which is amplified in the amplifier and transmitted into the lug boss, and the amplified compression stress wave is reflected by the free end surface of the lug boss as a tension wave and forms an incident wave of the Hopkinson tension bar. The incident wave is transmitted into the incident bar of the Hopkinson tension bar. When the incident wave is transmitted to the contact surface between the incident bar and the sample, because the wave impedances are mismatched, one part of the incident wave is reflected to form a reflected wave in the incident bar, and the other part is transmitted into the transmission bar through the sample to form a transmitted wave. The shape and the amplitude of the reflected wave and the transmitted wave depend on the material property of the sample. The data acquisition unit records signals of the incident wave and the reflected wave through the strain gage pasted on the incident bar, and records signals of the transmitted wave through the strain gage pasted on the transmission bar. The signals of the reflected wave and the reflected recorded by the data acquisition unit are used to obtain a dynamic tension stress strain curve of material by a one-wave method.

In the present invention, a stress wave generator is composed of a loading gun and a power supply system. The power supply system is used for supplying instantaneous strong current to the primary coil of the loading gun so as to cause strong electromagnetic repulsion to be generated between the primary coil and the secondary coil. The loading gun is composed of a loading gun housing, a primary coil, a secondary coil, a centering tube and an amplifier, and is used for generating electromagnetic repulsion, converting the electromagnetic repulsion to a stress wave and outputting the stress wave amplified by a tapered amplifier to the Hopkinson bar.

In the present invention, the stress wave is directly generated through electromagnetic repulsion, a primary coil and a secondary coil are arranged in the loading gun, the primary coil is fixed to the loading gun housing and located in the middle section of the loading gun housing, a through hole is formed at the center of the primary coil, and a centering tube is installed for locating the compression head or the tension head; the secondary coil is a copper disk, is fixedly connected with a tapered amplifier for generating compression wave or tension wave, and is close to the primary coil. The primary coil and the amplifier are coaxial, and the coaxiality thereof is determined through the centering tube. When the compression experiment is performed, the pressure bar system and the amplifier are located at the same side of the primary coil, the compression head is screwed into the threaded hole of the amplifier through thread fit, and the end surface not screwed into the amplifier is fitted with the incident end of the pressure bar; when the tension experiment is performed, the pressure bar system and the amplifier are located at the two sides of the primary coil, and the thread end of the incident bar of the Hopkinson tension bar passes through the centering tube and is in threaded connection with the lug boss of the tension head. During experiments, strong changing current passes through the primary coil which will generate strong changing magnetic field, the strong changing magnetic field will generate induced current in the secondary coil, the direction of the induced magnetic field generated by the induced current is opposite to that of the magnetic field of the primary coil, and then electromagnetic repulsion is generated between the primary coil and the secondary coil; the electromagnetic repulsion is showed as a compression stress wave in the secondary coil, and the compression stress wave is amplified by the tapered amplifier; if the compression head is fitted with the end surface of the incident bar of the Hopkinson pressure bar, the compression stress wave in the compression head is directly transmitted into the incident bar of the Hopkinson pressure bar, and then the compression test may be performed on the material; if the incident end of the tension bar penetrates through the primary coil and the amplifier at the other side, and the lug boss is in threaded connection with the incident bar, and the compression wave in the amplifier is converted into a tension wave with equal amplitude after being reflected in the lug boss and is changed in the transmission direction to be transmitted into the incident bar of the Hopkinson tension bar, so that dynamic tension loading may be carried out on the material. Therefore, this device may be used for conducting compression experiment and tension experiment on the material.

The power supply is provided for the primary coil through discharging of the capacitor; because the capacitor has short discharging time and strong discharging current, strong instantaneous repulsion may be generated between the primary coil and the secondary coil so as to generate strong stress pulse. The technology of a charging and discharging control system of the capacitor is very mature in the electromagnetic riveting apparatus at present, and may be used directly.

The lug boss is in threaded connection with the incident bar of the Hopkinson tension bar, and the compression head is in tight fit with the end surface of the incident bar of the Hopkinson bar so that the output stress wave is steadily transmitted into the experimental system. In the experiment device of the present invention, stress pulse is directly generated through the electromagnetic repulsion between the primary coil and the secondary coil in the loading gun and is transmitted into the incident bar so that the generated pulse signals may be accurately controlled according to the needs of experimenters.

The amplitude of the stress wave actually generated in the present invention may be controlled through the charging voltage of the electromagnetic riveting apparatus, and the width of the stress wave actually generated may be controlled by adjusting the capacitance value of the electromagnetic riveting apparatus.

Through the electromagnetic induction principle, the present invention may not only generate compression stress wave, but also may generate tension stress wave, and may be applied to the loading of the Hopkinson tension bar and pressure bar. The loading systems of the Hopkinson tension bar and pressure bar may be realized on the same apparatus at the same time, which overcomes the defect that the previously proposed Hopkinson bar loading device based on the electromagnetic riveting apparatus only may conduct tension or compression independently. Compared with the solution proposed in the patents with the patent No. 201410173843.1 and 201410171963.8, the stress wave generator proposed in the present invention has simpler structure and still can adopt the waveform shaping technology of the traditional Hopkinson tension bar under the tension condition.

In the present invention, electromagnetic induction repulsion and capacitor discharging are combined in principle to replace the air gun and bullets in the traditional split Hopkinson bar system to directly generate stress pulse. The material may be loaded under the expected amplitude and pulse width using the traditional Hopkinson bar sample. The whole system of the device is simple in operation and strong in controllability. Because the stress wave is controlled in an electromagnetic mode, the amplitude of the output stress wave corresponding to the same voltage is constant when the capacitance value of the capacitor charger is constant, and the width of the stress wave corresponding to the same capacitance value is constant when the charging voltage is constant, so the stress wave may be accurately controlled, and the repeatability of the experiment is good; secondly, because the stress wave is generated through electromagnetic loading, the width of the stress pulse is not as limited by the length of an impact bar as the traditional impact mode, and for the low-strain rate experiment, the strain that the present invention may reach is larger than that of the traditional Hopkinson bar. For example, the present invention can generate stress wave with the pulse width of 0.50 ms. If the stress wave is used for conducting a compression test on the sample at the strain rate of 100 $s^{-1}$, the maximum strain that the sample may reach is 0.05, while it is difficult for the traditional Hopkinson bar to reach such a low strain rate, even this strain rate may be reached using bullets of 0.8 m, the width of the generated stress pulse is 0.32 ms, and the maximum strain reached by the sample is 0.032 which is obviously lower than that reached by the electromagnetic loading Hopkinson bar. With the above advantages, the device and the method of the present invention realize the strain rate and the strain range that the traditional split Hopkinson bar experiment cannot reach, standardize the Hopkinson bar experimental technology and integrate the experiment apparatus of the tension bar and the pressure bar, thus reducing the complexity of the apparatus and saving occupation space.

DESCRIPTION OF DRAWINGS

FIG. 4a is a front view and FIG. 4b is a view A-A of FIG. 4a.

FIG. 5 is a structural schematic diagram of a centering tube, wherein FIG. 5a is a front view, and FIG. 5b is a side view of FIG. 5a.

FIG. 6 is an assembly diagram of an amplifier.

FIG. 7 is a schematic diagram of the structure size of a compression head, wherein FIG. 7a is a front view, and FIG. 7b is a view A-A of FIG. 7a.

FIG. 8 is an assembly diagram of a compression experiment amplifier.

FIG. 9 is an assembly diagram of a tension experiment amplifier.

1. Resistor; 2. Transformer; 3. Rectifier; 4. Capacitor; 5. Electronic switch; 6. Loading gun; 7. Housing; 8. Primary coil; 9. Centering tube; 10. Secondary coil; 11. Insulation layer; 12. Amplifier; 13. Compression head; 14. Strain gage; 15. Incident bar; 16. Sample; 17. Transmission bar; 18.

Buffer; 19. Data acquisition unit; 20. Power supply; 21. Capacitor charger; 22. Lug boss; 23. Lead.

DETAILED DESCRIPTION

Embodiment 1

This embodiment relates to a Hopkinson pressure/tension bar stress wave generator based on electromagnetic force, comprising a power supply 20, a capacitor charger 21 and a loading gun 6, A power supply part of the existing electromagnetic riveting apparatus is used by the capacitor charger 21, and a positive electrode output line of the output of the capacitor charger 21 is connected with a positive electrode line of the loading gun 6 and a negative electrode output line thereof is connected with a negative electrode line of the loading gun 6. The power supply 20 uses three-phase alternating current of 220V.

In this embodiment, the power supply part of the existing electromagnetic riveting apparatus published in the patent with the patent No. 200520079179 is used by the capacitor charger 21. In this embodiment, ten electrolytic capacitors with the rated voltage of 1000 volts and rated capacitance of 2000 microfarad are connected in parallel to form a capacitor group, the capacitor group and an electronic switch are installed in a capacitor cabinet to control the discharging of the capacitor group through the electronic switch. The control cabinet mainly contains a PLC and a control system thereof. The control system mainly consists of an analog control part, a digital control part and a digital display part, wherein the analog control part uses a TCA785 chip of SIEMENS corporation; the digital control part consists of a CPU224 of S7-200 series of SIEMENS and an analog input output extension module EM235 of SIEMENS; the charging voltage is mainly controlled in the PID control mode of voltage loop and current loop; and the digital display part mainly consists of text displays TD200 of S7-200 series.

Figure 1:
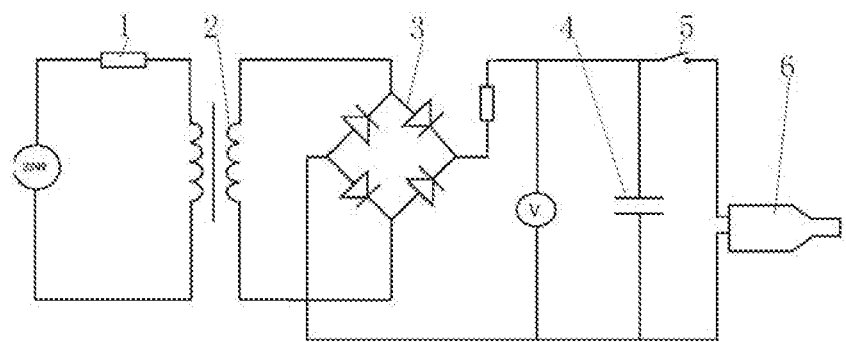
FIG. 1 is a schematic diagram of a Hopkinson pressure/tension bar stress wave generator based on an electromagnetic force.
Figure 2:
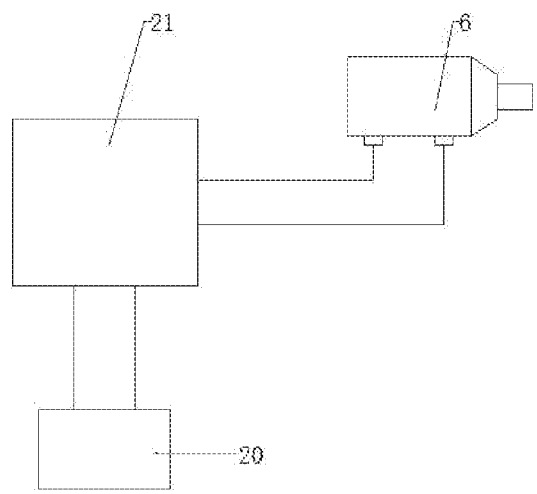
FIG. 2 is a structural schematic diagram of a Hopkinson pressure/tension bar stress wave generator based on an electromagnetic force.
Figure 3:
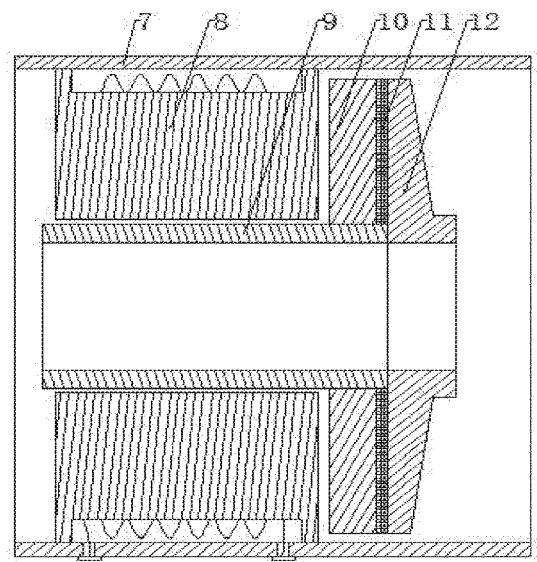
FIG. 3 is a schematic diagram of an internal structure of a loading gun, wherein a housing is split along symmetry planes.
Figure 4:
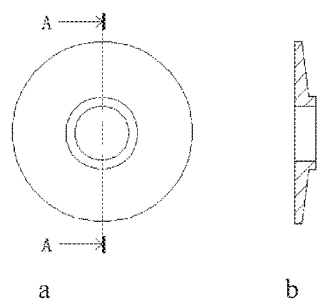
FIG. 4 is a structural schematic diagram of an amplifier, where
Figure 5:
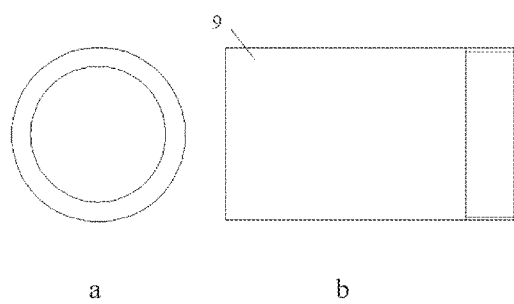

As shown in FIG. 3, the loading gun comprises a loading gun housing 7, a primary coil 8, a centering tube 9, a secondary coil 10, an insulation layer 11 and an amplifier 12. The loading gun housing 7 is used as a carrier. The primary coil 8 and the secondary coil 10 are mounted on the centering tube in sequence, and one end surface of the secondary coil 10 is made to be adjacent to a locating end surface of the centering tube; and the other end surface of the secondary coil 10 is made to be adjacent to and freely fitted with one end surface of the primary coil 8.

The centering tube on which the primary coil 8 and the secondary coil 10 are mounted is put in the middle section in the loading gun housing, the amplifier 12 is installed at one end of the centering tube, and the insulation layer 11 is mounted between the internal end surface of the amplifier and the end surface of the secondary coil.

The primary coil 8, the secondary coil 10, the amplifier 12 and the centering tube 9 are all coaxial to the loading gun housing.

The centering tube is mutually matched with an internal thread of the secondary coil 10 through the external thread located at one end of the centering tube, and the centering tube is fixedly connected with the secondary coil, to be used for transmitting the tension stress wave and also be used for locating the primary coil 8, the secondary coil 10 and the amplifier 12.

In this embodiment, the loading gun housing 7 is made of nylon with good insulating property. The primary coil 8 of the loading gun wound around a core with an I-shaped cross section using a 25-mm-wide and 1-mm-thick copper strip, and every two turns of the copper strip are separated from each other by art insulation material. The external diameter of the primary coil 8 is identical to the internal diameter of the loading gun housing 7, and after the primary coil 8 is put in the loading gun housing 7, the primary coil 8 and the loading gun housing 7 are in interference fit.

The secondary coil 10 is a copper disk, and a threaded through hole in fit with the centering tube 9 is formed at the center of the secondary coil.

The amplifier 22 is a hollow gyrator. The internal surface of the central hole of the amplifier is a threaded surface matched with the external thread of the compression head 13. The internal diameter of the central hole of the amplifier is slightly larger than the external diameter of the incident bar 15 of the Hopkinson tension bar, and after the incident bar 15 of the Hopkinson tension bar is put in the central hole, the incident bar of the Hopkinson tension bar and the central hole are in clearance fit.

The external circumference surface of the amplifier 12 is of a step shape, comprising isometric sections at both ends of the amplifier and a conic section at the center of the amplifier. For the isometric sections at the two ends of the amplifier 12, the isometric section having the maximum external diameter at one end of the amplifier is a stress wave receiving section; and the isometric section having the minimum external diameter at the other end of the amplifier is a stress wave output section. The conic section that transitionally connects the two isometric sections forms a stress wave amplification reflection section of the amplifier. The external diameter of the stress wave receiving section of the amplifier is the same as that of the secondary coil. The ratio of the diameter of the stress wave receiving section to the diameter of the stress wave output section of the amplifier equals to 5:2; and the ratio of the axial length of the large external diameter section to that of the conic section of the amplifier equals to 1:1.

The lug boss 22 is a hollow gyrator. The internal surface of the lug boss is a threaded surface matched with the threaded end of the Hopkinson tension bar. While in use, the lug boss 22 is mounted on the incident bar 15, and is located on the end surface at one end of the stress wave amplification reflection section of the amplifier 12. The lug boss is used for reflecting the compression wave transmitted by the amplifier into a tension wave and transmitting same into the tension bar. When a tension test is performed, the incident bar 15 of the Hopkinson tension bar penetrates through the through hole of the centering tube 9 and the threaded hole of the amplifier 12 in sequence and is in threaded connection with the lug boss 22, and is freely matched with the threaded hole of the amplifier 12 and the through hole of the centering tube 9 in dimension. In this embodiment, the axial length of the lug boss is 5 mm, and the external diameter thereof is 20 mm.

The compression head 13 is a gyrator. The external circumference surface of the compression head is of a two-step shape, wherein the large-diameter section is the compression wave output section, and the small-diameter section is connection section. The external circumference surface of the compression wave output section is symmetrically provided with planes. In this embodiment, the axial length of the compression wave output section is 5 mm, the diameter is 16 mm, and the symmetry planes of the external circumference surface are obtained by respectively cutting off ¼ circular arc from the circle surfaces at both sides of the compression wave output section. When test is performed, the connection section of the compression head 13 is put in the internal threaded hole of the amplifier 12, and the compression head is in threaded connection with the amplifier 12. The internal end surface of the compression wave output section of the compression head is in contact with the incident bar, thereby transmitting the stress waves into the incident bar. In this embodiment, the connection section of the compression head includes the external thread of M1.5, and the axial length thereof is 5 mm.

The wave impedance of the compression wave output section is identical to that of the Hopkinson pressure bar, and the wave impedance R is defined as:

$$W = \rho C A$$

where $\rho$ represents the density of material, C represents the stress wave velocity of material, and A represents the cross-sectional area.

When a compression test is performed, the compacting head 13 is located at one side in the loading gun housing, and is connected with the internal threaded hole at the center of the amplifier 12 through the connection section at one end of the compression head. When a tension test is performed, the threaded end of the incident bar 15 of the Hopkinson tension bar penetrates through the through holes of the centering tube 9 and the amplifier 12 in sequence, and is in threaded connection with the lug boss 22 at one side of the stress wave output section of the amplifier 12. The insulation layer 11 made of nylon is mounted on the centering tube and is fitted with the internal surface of the tension head 22 or the compaction head 13, and the induced eddy current generated in the secondary coil 10 is prevented from being transmitted into the amplifier 12 by the insulation layer 11. The secondary coil 10 is mounted on the centering tube through threads and is located on the internal side of the insulation layer. Two through holes are provided in the circumference surface at the same side of the loading gun housing 7, and two external connectors of the primary coil 8 respectively penetrate through one of the through holes and are fixed to the external surface of the loading gun housing 7. The positive electrode connector of the two external connectors of the primary coil 8 is connected with the positive electrode output line of the capacitor charger 21, and the negative electrode connector of the two external connectors is connected with the negative electrode output line of the capacitor charger 21.

The power supply 20, the incident bar 15, the transmission bar 17, the sample 16, the strain gage 14, the data acquisition unit 19 and the buffer 18 in this embodiment all use the prior art.

This embodiment also proposes an experiment method for a Hopkinson pressure/tension bar stress wave generator based on electromagnetic force. The Lu experiment method for the Hopkinson pressure/tension bar stress wave generator based on electromagnetic force comprises a Hopkinson compression experiment and a Hopkinson tension experiment.

I. The specific process of the Hopkinson compression experiment on the Hopkinson pressure/tension bar stress wave generator based on electromagnetic force comprises:

Step 1: Arranging Equipment;

The loading gun 6, the incident bar 15 and the transmission bar 17 are installed on an experiment rig in a coaxial sequence according to a conventional method, and the incident bar 15 and the transmission bar 17 are configured to freely move in the axial direction. A sample 16 is installed between the incident bar 15 and the transmission bar 17, and the sample 16 is configured to be coaxial with the incident bar 15 and the transmission bar 17.

Step 2: Pasting Strain Gages:

The strain gages are pasted by using the existing technology, i.e. two strain gages with identical parameters are symmetrically pasted on the surfaces of the incident bar and the transmission bar by using the axis of the incident bar or the transmission bar as a symmetry axis on the circumference at half length of the incident bar 15 or the transmission bar 17, and strain gage leads 23 are welded on pins of the strain gages and connected with a Wheatstone bridge in the data acquisition system.

Figure 10:
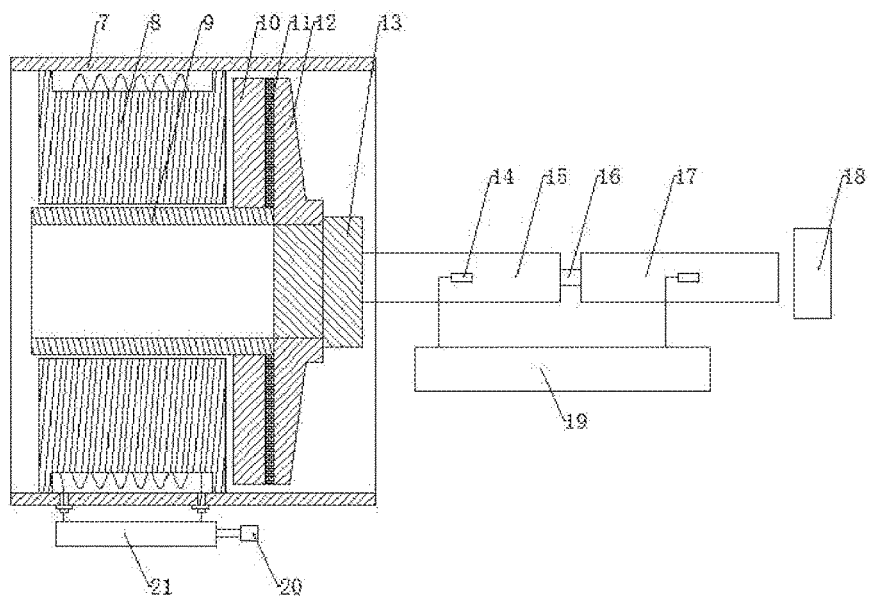
FIG. 10 is a schematic diagram of a compression experiment.
Figure 11:
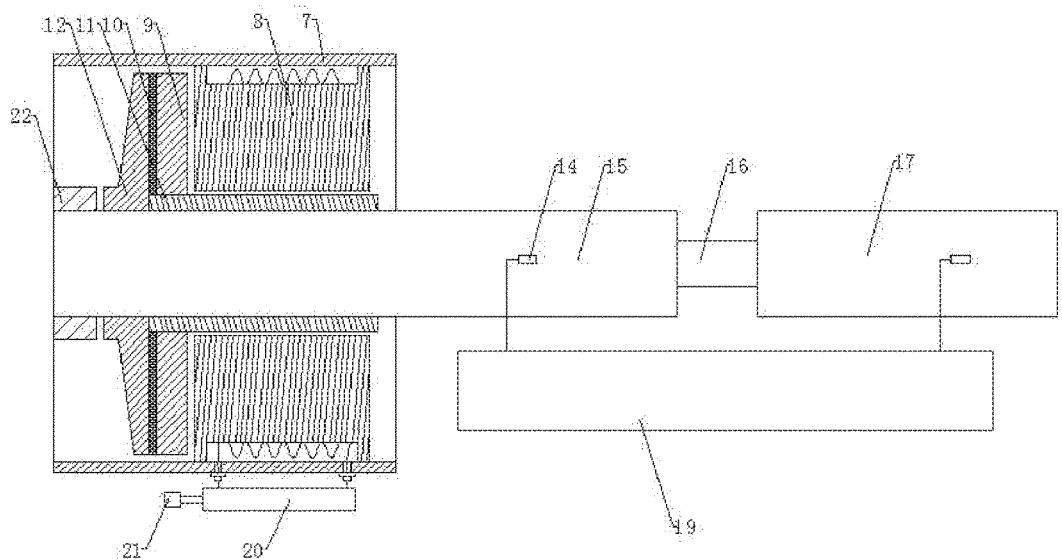
FIG. 11 is a schematic diagram of a tension experiment.
Figure 12:
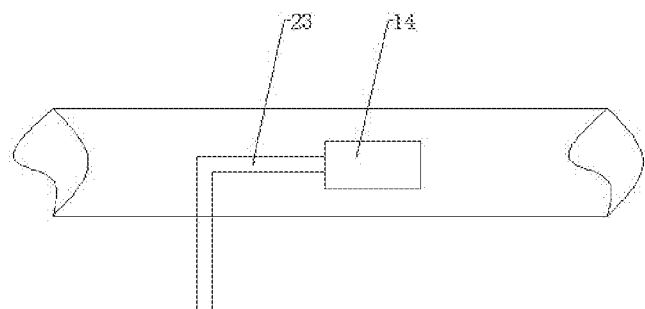
FIG. 12 shows a distribution method of strain gage leads.
Figure 13:
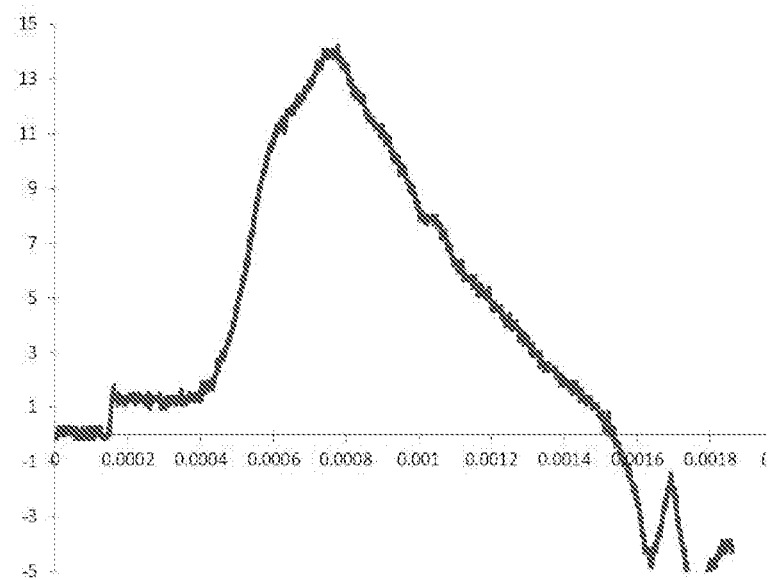
FIG. 13 shows a stress signal detected by a general distribution method of strain gage leads, wherein abscissa represents time in s, and ordinate represents stress in Mpa.
Figure 14:
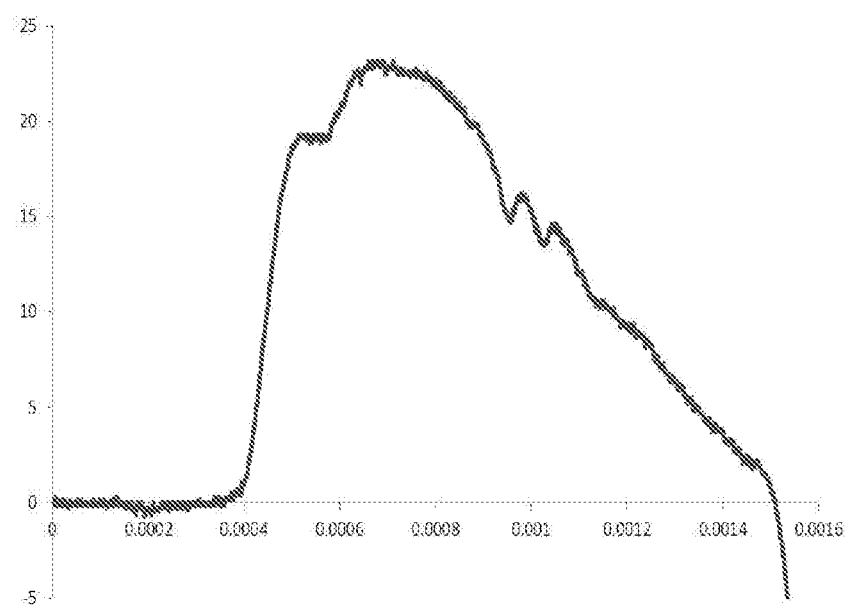
FIG. 14 shows a stress signal detected by a distribution method of strain gage leads of the present invention, where abscissa represents time in s, and ordinate represents the stress in Mpa. In the drawings.

The arrangement of strain gage leads 23 has special requirements; otherwise, the data acquisition unit 19 is not able to normally collect experimental data due to electromagnetic interference. If the projection of the strain gage leads 23 on the plane that is perpendicular to the axis of the incident bar or the transmission bar forms a closed loop, changing magnetic field lines may penetrate through the loop formed by the strain gage leads 23 when a high magnetic field is generated due to discharging of the loading gun 6, which generates changing magnetic flux in the loop, thereby forming induced current to interfere with the data acquisition unit 19, making the data collected unusable. The solution to the problem is that as shown in FIG. 8, the strain gage leads 23 are first distributed in parallel with the axis of the incident bar or the transmission bar and then led out after being bent at a right angle with the axial direction so that the leads are connected with the data acquisition unit 19 in straight line, and therefore the leads will not generate induced currents due to the change in magnetic flux. As shown in FIGS. 9 and 10, the stress wave signal interference measured by the general distribution method of strain gage leads is very large, while the stress wave signal interference measured by the distribution method of strain gage leads proposed in the present invention is completely eliminated.

Step 3: Loading and Processing Data:

As shown in FIG. 6, when the Hopkinson compression experiment is performed, the compression head 13 connected with the amplifier 12 through existing threads, the centering tube 9 passes through a through hole of the primary coil, and the end, provided with the compression head 13, of the loading gun 6 is close to the incident bar. The stress wave output section of the compression head 13 is coaxially and fully fitted with the end surface of the incident bar 115 of the Hopkinson pressure bar. After the capacitor charger 21 is charged, the capacitor charger discharges to the primary coil 8 of the loading gun 6 to generate electromagnetic repulsion between the secondary coil 10 and the primary coil 8, the electromagnetic repulsion is showed as a compression stress wave in the amplifier 12 and forms an incident wave after being amplified by the amplifier 12, and the incident wave is transmitted into the incident bar 15 of the Hopkinson pressure bar through the compression head 13. When the incident wave is transmitted to the contact surface between the incident bar 15 and the sample 16, because the wave impedances are mismatched, one part of the incident wave is reflected to form a reflected wave in the incident bar 15, and the other part is transmitted into the transmission bar 17 through the sample 16 to form a transmitted wave. The shape and the amplitude of the reflected wave and the transmitted wave depend on the material property of the sample 16.

The data acquisition unit 19 records the signals of the incident wave and the reflected wave through the strain gage 14 pasted on the incident bar 15, and records the signals of the transmitted wave through the strain gage 14 pasted on the transmission bar 17. The signals of the reflected wave and transmitted wave recorded by the data acquisition unit 19 are used to obtain a dynamic compression stress strain curve of a specimen by a one-wave method.

II. The specific process of the Hopkinson tension experiment performed on the Hopkinson pressure/tension bar stress wave generator based on electromagnetic force comprises:

Step 1: Arranging equipment: the loading gun 6, the incident bar 15 and the transmission bar 17 are installed on an experiment rig in a coaxial sequence according to a conventional method, and the incident bar 15 and the transmission bar 17 are made to only freely move in the axial direction. The end, provided with the compression head 13, of the loading gun 6 is close to the incident bar 15. A sample 16 is installed between the incident bar 15 and the transmission bar 17, and the sample 16 is made to be coaxial to the incident bar 15 and the transmission bar 17.

Step 2: Pasting strain gages: the strain gages are pasted by using the existing technology, i.e. two strain gages with identical parameters are symmetrically pasted on the surface of the incident bar or the transmission bar by using the axis of the incident bar or the transmission bar as a symmetry axis on the circumference at half length of the incident bar 15 or the transmission bar 17, and strain gage leads 23 are welded on pins of the strain gages and connected with a Wheatstone bridge in the data acquisition system.

The arrangement of strain gage leads 23 has special requirements; otherwise, the data acquisition unit 19 is not able to normally collect experimental data due to electromagnetic interference. If the projection of the strain gage leads 23 on the plane that is perpendicular to the axis of the incident bar or the transmission bar forms a closed loop, changing magnetic field lines may penetrate through the loop formed by the strain gage leads 23 when a high magnetic field is generated due to discharging of the loading gun 6, which generates changing magnetic flux in the loop, thereby forming induced current to interfere with the data acquisition unit 19, making the data collected unusable. The solution to the problem is that as shove in FIG. 8, the strain gage leads 23 are first distributed in parallel with the axis of the incident bar or the transmission bar and then led out after being bent at a right angle with the axial direction so that the leads are connected with the data acquisition unit 19 in straight line, and therefore the lead will not generate induced currents due to the change in magnetic flux. As shown in FIGS. 9 and 10, the stress wave signal interference measured by the general distribution method of strain gage leads is very large, while the stress wave signal interference measured by the distribution method of strain gage leads proposed in the present invention is completely eliminated.

Step 3: Loading and collecting data: as show in FIG. 7, the centering tube 9 penetrates through a through hole of the primary coil 8, and the amplifier 12 and the incident bar 15 are respectively located at both ends of the primary coil 8. The incident end of the incident bar 15 penetrates through a through hole of the centering tube 9 and a threaded hole of the amplifier 12, to freely mate with the threaded hole of the amplifier 12 and the through hole of the centering tube 9, the end, with an external thread, of the incident bar 15 passes through the amplifier and is in threaded connection with the lug boss 21. The charging voltage of the capacitor charger 21 is set to 200V, and the capacitor charger is charged. After completion of charging, the capacitor charger discharges to the primary coil 8 of the loading gun through the electronic switch to generate electromagnetic repulsion between the secondary coil 10 and the primary coil primary coil 8, and the electromagnetic repulsion is amplified by the amplifier 12, is showed as a compression stress wave, is reflected by the lug boss 22 as a tension wave, and forms an incident wave of the Hopkinson tension bar. The incident wave is transmitted into the incident bar 15 of the Hopkinson tension bar. When the incident wave is transmitted to the contact surface between the incident bar 15 and the sample 16, because the wave impedances are mismatched, one part of the incident wave is reflected to form a reflected wave in the incident bar 15, and the other part is transmitted into the transmission bar 17 through the sample 16 to form a transmitted wave. The shape and the amplitude of the reflected wave and the transmitted wave depend on the material property of the sample.

The data acquisition unit 19 records the signals of the incident wave and the reflected wave through the strain gage 14 pasted on the incident bar 15, and records the signals of the transmitted wave through the strain gage 14 pasted on the transmission bar 17. The signals of the reflected wave and transmitted wave recorded by the data acquisition unit 19 are used to obtain a dynamic tension stress strain curve of material through a one-wave method.

Embodiment 2

This embodiment relates to a Hopkinson pressure/tension bar stress wave generator based on electromagnetic force, comprising a power supply 20, a capacitor charger 21 and a loading gun 6. A power supply part of the existing electromagnetic riveting apparatus is used by the capacitor charger 21, and a positive electrode output line of the output of the capacitor charger 21 is connected with a positive electrode line of the loading gun 6 and a negative electrode output line thereof is connected with a negative electrode line of the loading gun 6. The power supply 20 uses three-phase alternating current of 220V.

In this embodiment, the power supply part of the existing electromagnetic riveting apparatus published in the patent with the patent No. 200520079179 is used by the capacitor charger 21. In this embodiment, ten electrolytic capacitors with the rated voltage of 1000 volts and rated capacitance of 2000 microfarad are connected in parallel to form a capacitor group, and the capacitor group and an electronic switch are installed in a capacitor cabinet to control the discharging of the capacitor group through the electronic switch. The control cabinet mainly contains a PLC and a control system thereof. The control system mainly consists of an analog control part, a digital control part and a digital display part, wherein the analog control part uses a TCA785 chip of SIEMENS corporation; the digital control part consists of a CPU224 of S7-200 series of SIEMENS and an analog input output extension module EM235 of SIEMENS, the charging voltage is mainly controlled in the PID control mode of voltage loop and current loop; and the digital display part mainly consists of text displays TD200 of S7-200 series.

As shown in FIG. 3, the loading gun comprises a loading gun housing 7, a primary coil 8, a centering tube 9, a secondary coil 10, an insulation layer 11 and an amplifier 12. The loading gun housing 7 is used as a carrier. The primary coil 8 and the secondary coil 10 are mounted on the centering tube in sequence, and one end surface of the secondary coil 10 is made to be adjacent to a locating end surface of the centering tube; and the other end surface of the secondary coil 10 is made to be adjacent to and freely fitted with one end surface of the primary coil 8.

The centering tube on which the primary coil 8 and the secondary coil 10 are mounted is put in the middle section in the loading gun housing, the amplifier 12 is installer, at one end of the centering tube, and the insulation layer 11 is mounted between the internal end surface of the amplifier and the end surface of the secondary coil.

The primary coil 8, the secondary coil 10, the amplifier 12 and the centering tube 9 are all coaxial to the loading gun housing.

The centering tube 9 is mutually matched with the internal thread of the secondary coil 10 through the external thread located at one end of the centering tube, and the centering tube is fixedly connected with the secondary coil, to be used for transmitting the tension stress wave and also be used for locating the primary coil 8, the secondary coil 10 and the amplifier 12.

In this embodiment, the loading gun housing 7 is made of nylon with good insulating property. The primary coil 8 of the loading gun is wound around a core with an I-shaped cross section using a copper conducting wire of 10 mm in diameter, and every two turns of the copper conducting wire are separated from each other by an insulation material. The external diameter of the primary coil 8 is identical to the internal diameter of the loading gun housing 7, and after the primary coil 8 is put in the loading gun housing 7, the primary coil 8 and the loading gun housing 7 are in interference fit.

The secondary coil 10 is a copper disk, and is provided with a threaded through hole matched with the centering tube 9 in the center thereof.

The amplifier 22 is a hollow gyrator. The internal surface of the central hole of the amplifier is a threaded surface matched with the external thread of the compression head 13. The internal diameter of the central hole of the amplifier is slightly larger than the external diameter of the incident bar 15 of the Hopkinson tension bar, and after the incident bar 15 of the Hopkinson tension bar is put in the central hole, the incident bar 15 of the Hopkinson tension bar and the central hole are in clearance fit.

The external circumference surface of the amplifier 12 is of a step shape, comprising isometric sections at both ends of the amplifier and a conic section at the center of the amplifier. For the isometric sections at the two ends of the amplifier 12, the isometric section having the maximum external diameter at one end of the amplifier is a stress wave receiving section; the isometric section having the minimum external diameter at the other end of the amplifier is a stress wave output section. The conic section that transitionally connects the two isometric sections forms a stress wave amplification reflection section of the amplifier. The external diameter of the stress wave receiving section of the amplifier is the same as that of the secondary coil. The ratio of the diameter of the stress wave receiving section of the amplifier to the diameter of the stress wave output section equals to 5:2; and the ratio of the axial length of the large external diameter section of the amplifier to the axial length of the conic section equals to 1:1.

The lug boss 22 is a hollow gyrator. The internal surface of the lug boss is a threaded surface matched with the threaded end of the Hopkinson tension bar. While in use, the lug boss 22 is mounted on the incident bar 15, and is located on the end surface at one end of the stress wave amplification reflection section of the amplifier 12. The lug boss is used for reflecting the compression wave transmitted by the amplifier into a tension wave and transmitting same into the tension bar. When a tension test is performed, the incident bar 15 of the Hopkinson tension bar penetrates through the through hole of the centering tube 9 and the threaded hole of the amplifier 12 in sequence and is in threaded connection with the lug boss 22, and is freely matched with the threaded hole of the amplifier 12 and the through hole of the centering tube 9 in dimension. In this embodiment, the axial length of the lug boss is 5 mm, and the external diameter thereof is 20 mm.

The compression head 13 is a gyrator. The external circumference surface of the compression head is of a two-step shape, wherein the large-diameter section is the compression wave output section, and the small-diameter section is connection section. The external circumference surface of the compression wave output section is symmetrically processed with planes. In this embodiment, the axial length of the compression wave output section is 5 mm, the diameter is 16 mm, and the symmetry planes of the external circumference surface are obtained by respectively cutting off ¼ circular arc from the circle surfaces at both sides of the compression wave output section. When test is performed, the connection section of the compression head 13 is put in the internal threaded hole of the amplifier 12, and the compression head is in threaded connection with the amplifier 12. The internal end surface of the compression wave output section of the compression head is in contact with the incident bar, thereby transmitting the stress waves into the incident bar. In this embodiment, the connection section of the compression head includes the external thread of M15, and the axial length thereof is 5 mm.

The wave impedance of the compression wave output section is identical to that of the Hopkinson pressure bar, and the wave impedance R is defined as:

$$R=\rho CA$$

where $\rho$ represents the density of material, C represents the stress wave velocity of material, and A represents the cross-sectional area.

When a compression test is performed, the compacting head 13 is located at one side in the loading gun housing, and is connected with the internal threaded hole at the center of the amplifier 12 through the connection section at one end of the compression head. When a tension test is performed, the threaded end of the incident bar 15 of the Hopkinson tension bar penetrates through the through holes of the centering tube 9 and the amplifier 12 in sequence, and is in threaded connection with the lug boss 22 at one side of the stress wave output section of the amplifier 12. The insulation layer 11 made of nylon is mounted on the centering tube and is fitted with the internal surface of the tension head 22 or the compaction head 13, and the induced eddy current generated in the secondary coil 10 is prevented from being transmitted into the amplifier 12 by the insulation layer 11. The secondary coil 10 is mounted on the centering tube through threads and is located on the internal side of the insulation layer. Two through holes are provided in the circumference surface at the same side of the loading gun housing 7, and two external connectors of the primary coil 8 respectively penetrate through one of the through holes and are fixed to the external surface of the loading gun housing 7. The positive electrode connector of the two external connectors of the primary coil 8 is connected with the positive electrode output line of the capacitor charger 21, and the negative electrode connector of the two external connectors is connected with the negative electrode output line of the capacitor charger 21.

The power supply 20, the incident bar 15, the transmission bar 17, the sample 16, the strain gage 14, the data acquisition unit 19 and the buffer 18 in this embodiment all use the prior art.

This embodiment also proposes an experiment method for a Hopkinson pressure/tension bar stress wave generator based on electromagnetic force. The experiment method for the Hopkinson pressure/tension bar stress wave generator based on electromagnetic force comprises a Hopkinson compression experiment and a Hopkinson tension experiment.

I. The specific process of the Hopkinson compression experiment on the Hopkinson pressure/tension bar stress wave generator based on electromagnetic force comprises:

Step 1: Arranging Equipment;

The loading gun 6, the incident bar 15 and the transmission bar 17 are installed on an experiment rig in a coaxial sequence according to a conventional method, and the incident bar 15 and the transmission bar 17 are made to freely move in the axial direction. A sample 16 is installed between the incident bar 15 and the transmission bar 17, and the sample 16 is made to be coaxial to the incident bar 15 and the transmission bar 17.

Step 2: Pasting Strain Gages:

The strain gages are pasted by using the existing technology, i.e. two strain gages with identical parameters are symmetrically pasted on the surfaces of the incident bar and the transmission bar by using the axis of the incident bar or the transmission bar as a Symmetry axis on the circumference at half length of the incident bar 15 or the transmission bar 17, and strain gage leads 23 are welded on pins of the strain gages and connected with a Wheatstone bridge in the data acquisition system.

The arrangement of strain gage leads 23 has special requirements; otherwise, the data acquisition unit 19 is not able to normally collect experimental data due to electromagnetic interference. If the projection of the strain gage leads 23 on the plane that is perpendicular to the axis of the incident bar or the transmission bar forms a closed loop, changing magnetic field lines may penetrate through the loop formed by the strain gage leads 23 when a high magnetic field is generated due to discharging of the loading gun 6, which generates changing magnetic flux in the loop, thereby forming induced current to interfere with the data acquisition unit 19, making the data collected unusable. The solution to the problem is that as shown in FIG. 8, the strain gage leads 23 are first distributed in parallel with the axis of the incident bar or the transmission bar and then led out after being bent at a right angle with the axial direction so that the leads are connected with the data acquisition unit 19 in straight line, and therefore the lead will not generate induced currents due to the change in magnetic flux. As shown in FIGS. 9 and 10, the stress wave signal interference measured by the general distribution method of strain gage leads is very large, while the stress wave signal interference measured by the distribution method of strain gage leads proposed in the present invention is completely eliminated.

Step 3: Loading and Processing Data:

As shown in FIG. 6, when the Hopkinson compression experiment is performed, the compression head 13 connected with the amplifier 12 through existing threads, the centering tube passes through a through hole of the primary coil, and the end, provided with the compression head 13, of the loading gun 6 is close to the incident bar. The stress wave output section of the compression head 13 is coaxially and fully fitted with the end surface of the incident bar 15 of the Hopkinson pressure bar. After the capacitor charger 21 is charged, the capacitor charger discharges to the primary coil 8 of the loading gun 6 to generate electromagnetic repulsion between the secondary coil 10 and the primary coil 8, the electromagnetic repulsion is showed as a compression stress wave in the amplifier 12 and forms an incident wave after being amplified by the amplifier 12, and the incident wave is transmitted into the incident bar 15 of the Hopkinson pressure bar through the compression head 13. When the incident wave is transmitted to the contact surface between the incident bar 15 and the sample 16, because the wave impedances are mismatched, one part of the incident wave is reflected to form a reflected wave in the incident bar 15, and the other part is transmitted into the transmission bar 17 through the sample 16 to form a transmitted wave. The shape and the amplitude of the reflected wave and the transmitted wave depend on the material property of the sample 16.

The data acquisition unit 19 records the signals of the incident wave and the reflected wave through the strain gage 14 pasted on the incident bar 15, and records the signals of the transmitted wave through the strain gage 14 pasted on the transmission bar 17. The signals of the reflected wave and transmitted wave recorded by the data acquisition unit 19 are used to obtain a dynamic compression stress strain curve of a specimen by a one-wave method.

II. The specific process of the Hopkinson tension experiment performed on the Hopkinson pressure/tension bar stress wave generator based on electromagnetic force comprises:

Step 1: Arranging equipment: the loading gun 6, the incident bar 15 and the transmission bar 17 are installed on an experiment rig in a coaxial sequence according to a conventional method, and the incident bar 15 and the transmission bar 17 are made to only freely move in the axial direction. The end, provided with the compression head 13, of the loading gun 6 is close to the incident bar 15. A sample 16 is installed between the incident bar 15 and the transmission bar 17, and the sample 16 is made to be coaxial to the incident bar 15 and the transmission bar 17.

Step 2: Pasting strain gages: the strain gages are pasted by using the existing technology, i.e. two strain gages with identical parameters are symmetrically pasted on the surface of the incident bar or the transmission bar by using the axis of the incident bar or the transmission bar as a symmetry axis on the circumference at half length of the incident bar 15 or the transmission bar 17, and strain gage leads 23 are welded on pins of the strain gages and connected with a Wheatstone bridge in the data acquisition system.

The arrangement of strain gage leads 23 has special requirements; otherwise, the data acquisition unit 19 is not able to normally collect experimental data due to electromagnetic interference. If the projection of the strain gage leads 23 on the plane that is perpendicular to the axis of the incident bar or the transmission bar forms a closed loop, changing magnetic field lines may penetrate through the loop formed by the strain gage leads 23 when a high magnetic field is generated due to discharging of the loading gun 6, which generates changing magnetic flux in the loop, thereby forming induced current to interfere with the data acquisition unit 19, making the data collected unusable. The solution to the problem is that as shown in FIG. 8, the strain gage leads 23 are first distributed in parallel with the axis of the incident bar or the transmission bar and then led out after being bent at a right angle with the axial direction so that the leads are connected with the data acquisition unit 19 in straight line, and therefore the leads will not generate induced currents due to the variation in magnetic flux. As shown in FIGS. 9 and 10, the stress wave signal interference measured by the general distribution method of strain gage leads is very large, while the stress wave signal interference measured by measured by the distribution method of strain gage leads proposed in the present invention is completely eliminated.

Step 3: Loading and collecting data: as show in FIG. 7, the centering tube 9 penetrates through the through hole of the primary coil 8, and the amplifier 12 and the incident bar 15 are respectively located at both ends of the primary coil 8. The incident end of the incident bar 15 penetrates through a through hole of the centering tube 9 and a threaded hole of the amplifier 12 to freely match with the threaded hole of the amplifier 12 and the through hole of the centering tube 9, and the end, with an external thread, of the incident bar 15 passes through the amplifier and is in threaded connection with a lug boss 21. The charging voltage of the capacitor charger 21 is set to 200V, and the capacitor charger is charged. After completion of charging, the capacitor charger discharges to the primary coil 8 of the loading gun through the electronic switch to generate electromagnetic repulsion between the secondary coil 10 and the primary coil primary coil 8, and the electromagnetic repulsion is amplified by the amplifier 12, is showed as a compression stress wave, is reflected by the lug boss 22 as a tension wave, and forms an incident wave of the Hopkinson tension bar. The incident wave is transmitted into the incident bar 15 of the Hopkinson tension bar. When the incident wave is transmitted to the contact surface between the incident bar 15 and the sample 16, because the wave impedances are mismatched, one part of the incident wave is reflected to form a reflected wave in the incident bar 15, and the other part is transmitted into the transmission bar 17 through the sample 16 to form a transmitted wave. The shape and the amplitude of the reflected wave and the transmitted wave depend on the material property of the sample.

The data acquisition unit 19 records the signals of the incident wave and the reflected wave through the strain gage 14 pasted on the incident bar 15, and records the signals of the transmitted wave through the strain gage 14 pasted on the transmission bar 17. The signals of the reflected wave and the transmitted wave recorded by the data acquisition unit 19 are used to obtain a dynamic tension stress strain curve of material through a one-wave method.

What is claimed is:

1. A loading device, comprising:
   a loading gun that includes a loading gun housing;
   a centering tube positioned inside the loading gun housing, the centering tube defining a tube hole that extends from a first end of the centering tube to a second end of the centering tube, the first and second ends each being positioned in an interior of the loading gun housing and spaced apart from longitudinal ends of the loading gun housing;
   an amplifier positioned inside the loading gun housing adjacent the centering tube at the first end of the centering tube, the amplifier defining a threaded hole through the amplifier, the threaded hole being coaxial with the centering tube and aligned with the tube hole;
   a primary coil mounted on the centering tube;
   a secondary coil mounted on the centering tube between the primary coil and the amplifier, the secondary coil being threadedly connected to the centering tube, the secondary coil having an end surface that is adjacent to and freely fitted with an end surface of the primary coil; and
   an insulation layer mounted on the centering tube between the amplifier and the secondary coil.

2. The loading device of claim 1, wherein the centering tube, the primary coil, the secondary coil, and the amplifier are coaxial with the loading gun housing.

3. The loading device of claim 1, wherein the amplifier has an end surface facing the first end of the centering tube, the end surface having a larger external diameter than the centering tube.

4. The loading device of claim 3, wherein the end surface has an external diameter matched to an external diameter of the secondary coil.

5. The loading device of claim 4, herein the external diameters of the end surface and the secondary coil are less than an internal diameter of the loading gun housing, such that the end surface of the amplifier and the secondary coil are each spaced apart from an internal surface of the loading gun housing.

6. The loading device of claim 1, wherein in a cross-section taken parallel to a longitudinal axis of the centering tube, the amplifier has an external diameter that has:
   a first constant value for a first portion of the amplifier facing the insulation layer,
   a second constant value less than the first constant value for a second portion of the amplifier facing away from the insulation layer, and
   a linearly varying value between the first and second portions.

7. The loading device of claim 1, wherein:
   the primary coil is wound with a copper conductor on a core that has an I-shaped cross section;
   every two turns of the copper conductor are separated from each other by an insulation material;
   an exterior of the primary coil forms an interference fit with an internal surface of the loading gun housing; and
   the centering tube extends through a hole formed at the center of a core of the primary coil.

8. The loading device of claim 1, wherein:
   the secondary coil is a copper disk; and
   the secondary coil includes an interior threaded portion that mates with an exterior threaded portion of the centering tube.

9. The loading device of claim 1, further comprising a capacitor charger electrically coupled to the primary coil.

10. The loading device of claim 9, wherein:
    the capacitor charger is positioned outside the loading gun housing; and
    the capacitor charger connects to the primary coil through two holes spaced apart in the loading gun housing.

11. The loading device of claim 9, wherein:
    the secondary coil is not directly connected to the capacitor charger; and
    the secondary coil is configured to conduct eddy currents induced by the primary coil.

12. The loading device of claim 11, wherein the insulation layer is configured electrically insulate the amplifier from the eddy currents conducted in the secondary coil.

13. The loading device of claim 9, further comprising a power supply electrically coupled to the capacitor charger.

14. The loading device of claim 1, wherein the loading gun is configured to perform a compression test on a sample.

15. The loading device of claim 14, wherein:
    the amplifier is configured to threadedly connect to a compression head, such that at least one external thread on the compression head engages at least one internal thread on the amplifier.

16. The loading device of claim 1, wherein the loading gun is configured to perform a tension test on a sample.

17. The loading device of claim 16, wherein:
    the centering tube is configured to receive a portion of an incident bar that is insertable through the centering tube;
    the amplifier is configured to receive the portion of the incident bar that has been inserted through the centering tube, the portion being insertable through the amplifier without threadedly engaging the amplifier.

18. The loading device of claim 17, further comprising:
a lug boss positioned adjacent the amplifier, the amplifier being positioned between the lug boss and the centering tube, the lug boss having at least one internal thread that is configured to engage at least one external thread on the incident bar, the lug boss being configured to reflect a compression wave that has been transmitted by the amplifier into a tension wave and transmit the tension wave into the incident bar.

19. A method for performing a compression test on a sample, the method comprising:
positioning a loading gun, an incident bar, and a transmission bar in a coaxial arrangement, the incident bar and the transmission bar being freely movable in an axial direction;
positioning the sample between the incident bar and the transmission bar, such that the sample is coaxial with the incident bar and the transmission bar;
charging a capacitor charger;
discharging the capacitor charger to a primary coil of the loading gun to generate electromagnetic repulsion between the primary coil and a secondary coil of the loading gun, the electromagnetic repulsion producing a compression stress wave in an amplifier in the loading gun;
amplifying the compression stress wave with the amplifier to form an incident wave;
transmitting the incident wave into the incident bar;
propagating the incident wave through the incident bar to the sample, the sample transmitting a portion of the incident wave to the transmission bar, the sample reflecting a complementary portion of the incident wave back into the incident bar;
recording signals of the transmitted and reflected portions with strain gages coupled to the transmission bar and the incident bar, respectively; and
processing the recorded signals, with a processor, using a one-wave method to determine a dynamic compression stress strain curve of the sample.

20. A method for performing a tension test on a sample, the method comprising:
inserting an incident bar through a centering tube, then through an amplifier positioned at an end of the centering tube;
threadedly connecting the incident bar to a lug boss that is positioned adjacent the amplifier, the amplifier being positioned between the lug boss and the centering tube, such that at least one external thread on the incident bar engages at least one internal thread on the lug boss;
positioning the incident bar and a transmission bar in a coaxial arrangement, the transmission bar being freely movable in an axial direction;
positioning the sample between the incident bar and the transmission bar, such that the sample is coaxial with the incident bar and the transmission bar;
charging a capacitor charger;
discharging the capacitor charger to a primary coil of the loading gun to generate electromagnetic repulsion between the primary coil and a secondary coil of the loading gun, the electromagnetic repulsion producing a compression stress wave in the amplifier;
amplifying the compression stress wave with the amplifier to form an incident wave;
transmitting the incident wave into the incident bar;
propagating the incident wave through the incident bar to the sample, the sample transmitting a portion of the incident wave to the transmission bar, the sample reflecting a complementary portion of the incident wave back into the incident bar;
recording signals of the transmitted and reflected portions with strain gages coupled to the transmission bar and the incident bar, respectively; and
processing the recorded signals, with a processor, using a one-wave method to determine a dynamic compression stress strain curve of the sample.

* * * * *